US007563873B2

(12) United States Patent
Chien et al.

(10) Patent No.: US 7,563,873 B2
(45) Date of Patent: Jul. 21, 2009

(54) RABBIT MONOCLONAL ANTIBODIES TO HEPATITIS B SURFACE ANTIGENS AND METHODS OF USING THE SAME

(75) Inventors: David Ying Chien, Alamo, CA (US); Yiu-Lian Fong, Lafayette, CA (US); Azita Tabrizi, San Carlos, CA (US); Heather Todd, Vacaville, CA (US); Mark David Van Cleve, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 332 days.

(21) Appl. No.: 11/148,012

(22) Filed: Jun. 7, 2005

(65) Prior Publication Data

US 2006/0008798 A1 Jan. 12, 2006

Related U.S. Application Data

(60) Provisional application No. 60/583,734, filed on Jun. 28, 2004, provisional application No. 60/577,561, filed on Jun. 7, 2004.

(51) Int. Cl.
*C12P 21/08* (2006.01)

(52) U.S. Cl. .............. 530/387.3; 530/388.1; 530/389.4; 530/391.1

(58) Field of Classification Search ........................ None
See application file for complete search history.

(56) References Cited

U.S. PATENT DOCUMENTS

| | | | | |
|---|---|---|---|---|
| 4,722,840 | A | 2/1988 | Valenzuela et al. | |
| 4,859,595 | A * | 8/1989 | Strosberg et al. | 435/6 |
| 4,977,081 | A * | 12/1990 | Raybould et al. | 530/388.4 |
| 5,098,704 | A | 3/1992 | Valenzuela | |
| 5,324,513 | A | 6/1994 | Sobczak et al. | |
| 5,472,868 | A | 12/1995 | McCormack et al. | |
| 5,675,063 | A | 10/1997 | Knight | |
| 5,965,140 | A | 10/1999 | Valenzuela et al. | |
| 6,030,616 | A * | 2/2000 | Waters et al. | 424/149.1 |
| 6,306,625 | B1 | 10/2001 | Jacobs et al. | |

OTHER PUBLICATIONS

Paulij WP et al "Localization of a unique hepatitis B virus epitope sheds new light on the structure of hepatitis B virus surface antigen". J Gen Virol. Apr. 1999;80 ( Pt 8):2121-6.*

Bose B. et al. "Characterization and molecular modeling of a highly stable anti-Hepatitis B surface antigen scFv". Mol Immunol. Dec. 2003;40(9):617-31.*

Bruning A. et al. "A rapid chromatographic strip test for the pen-side diagnosis of rinderpest virus". J Virol Methods. Aug. 1999;81(1-2):143-54.*

NCBI Nucleotide Database, "Hepatitis B Surface Antigen Variant with Multiple Mutations in the a Determinant in an Agammaglobulinemic Patient," May 16, 1991, Accession No. AY341335.

NCBI Nucleotide Database, "Sequence analysis of hepatitis B virus genome of a new mutant of ayw subtype isolated in Sardinia," Jul. 14, 2003, Accession No. X59795.

NCBI Nucleotide Database, "A new immune escape mutant of hepatitis B virus with an Asp to Ala substitution of aa144 of the envelope major protein," Jul. 12, 1997, Accession No. AF013629.

Ashton-Rickhardt, et al., "Mutants of the hepatitis B virus surface antigen that define some antigen-ically essential residues in the immunodominant a region," J. Medical Virology (1989) 29(3):196-203.

Babcook et al., "A novel strategy for generating monoclonal antibodies from single, isolated lymph-ocytes producing antibodies of defined specificities," Proc. Natl. Acad. Sci. USA (1996) 93:7843-8.

Beames et al., "Insertions within the hepatitis B virus capsid protein influence capsid formation and RNA encapsidation," J. Virol. (1995) 69(11):6833-8.

Bimbaum et al., "Hepatitis B virus nucleocapsid assembly: primary structure requirements in the core protein," J. Virol. (1990) 64(7):3319-30.

Carman,W. Vaccine-associated mutants of hepatitis B virus. Viral Hepatitis and Liver Disease (1994) pp. 243-247, Eds: K. Nishioka, H. Suzuki, S. Mishiro T. Oda.

Carman WF, Zanetti AR, et.al., "Vaccine-induced escape mutant of hepatitus B virus," Lancet (1990) 336(8711):325-9.

Chien, Et Al., "Characterization of Rabbit Monoclonal Antibody Candidates for the Development of Improved Hepatitis B Virus (Hbc) Immunoassay for the Detection of Mutated Surface Antigens," Transfusion, vol. 44, Supplement, Sp177 (2004).

Norder et al., "Molecular basis of hepatitis B virus serotype variation within the four major subtype," J. General Virology (1992) 73(Pt 12):3141-5.

Fujii et al., "Gly 145 to Arg substitution in HBs antigen of immune escape mutant of hepatitis B virus," Biochem. Biophys Res Comm (1992) 184(3):1152-7.

Liguori et al., "Recombinant human interleukin-6 enhances the immunoglobulin secretion of a rabbit-rabbit hybridoma," Hybridoma (2001) 20(3):189-98.

Spieker-Polet et al., "Rabbit monoclonal antibodies: Generating a fusion partner to produce rabbit-rabbit hybridomas," Proc. Natl. Acad. Sci. USA (1995) 92:9348-52.

Valenzuela et al., "Nucleotide sequence of the gene coding for the major protein of hepatitis B virus surface antigen," (1979) Nature 280(5725):815-9.

Valenzuela et al., "Synthesis and assembly of hepatitis B virus surface antigen particles in yeast," (1982) Nature 298(5872):347-50.

(Continued)

*Primary Examiner*—Bo Peng
(74) *Attorney, Agent, or Firm*—Mei Hong; Roberta Robins; Robert Gorman

(57) ABSTRACT

Reagents, methods and immunodiagnostic test kits for the accurate detection of hepatitis B virus (HBV) infection are disclosed. The methods and kits employ novel rabbit monoclonal antibodies directed against HBV surface antigens (HBsAg) with mutations in the "a" determinant region of HBsAg.

9 Claims, 6 Drawing Sheets

OTHER PUBLICATIONS

Zhou et al., "Production of hepatitis B virus nucleocapsidlike core particles in Xenopus oocytes: assembly occurs mainly in the cytoplasm and does not require the nucleus," J. Virol. (1991) 65(10):5457-64.

Zuckerman et al., "Molecular epidemiology of hepatitis B virus mutants," (1999) J. Med Virol. 58(3):193-5.

Kuttner et al., "Characterization of Neutralizing Anti-Pre-S1 and Anti-Pre-S2 (HBV) and Monoclonal Antibodies and Their Fragments," Mol Immunol 36:669-683 (1999).

* cited by examiner

FIG. 1 (SEQ ID NO:1)
HBsAg "a" Determinant Mutant Sites
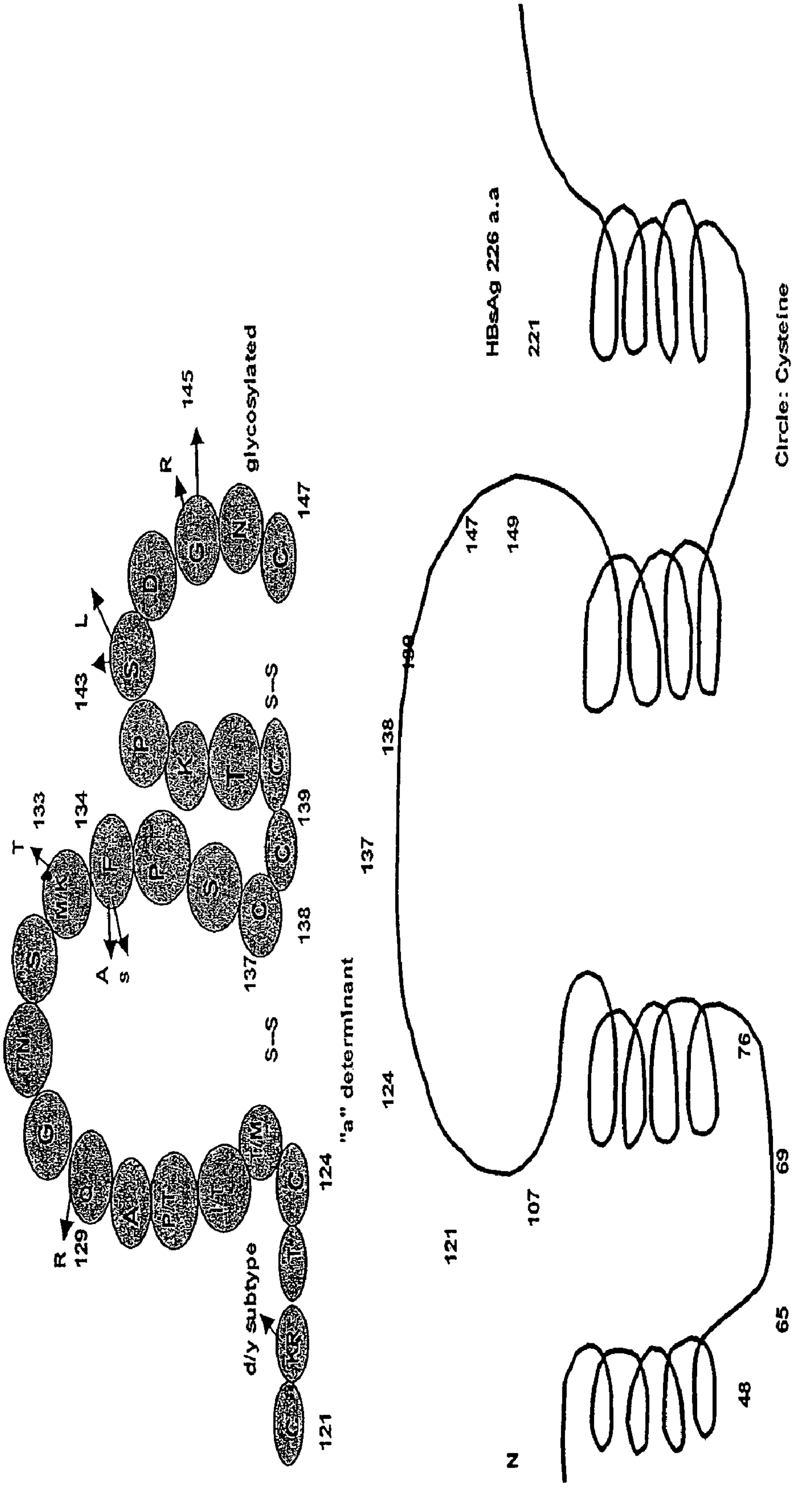

ADW WILD-TYPE

```
MENITSGFLGPLLVLQAGFFLLTRILTIPQSLDSWWTSLNFLGGSPVCLGQNSQSPTSNHSPTSCPP 67
ICPGYRWMCLRRFIIFLFILLLCLIFLLVLLDYQGMLPVCPLIPGTTTTSTGPCKTCTTPAQGNSMF 134
PSCCCTKPSDGNCTCIPIPSSWAFAKYLWEWASVRFSWLSLLVPFVQWFVGLSPTVWLSAIWMMWYW 201
GPSLYSIVSPFIPLLPIFFCLWVYI                                           226
```

A (SEQ ID NO:2)

AYW WILD-TYPE

```
MENITSGFLGPLLVLQAGFFLLTRILTIPQSLDSWWTSLNFLGGTTVCLGQNSQSPTSNHSPTSCPP 67
TCPGYRWMCLRRFIIFLFILLLCLIFLLVLLDYQGMLPVCPLIPGSSTTSTGPCRTCMTTAQGTSMY 134
PSCCCTKPSDGNCTCIPIPSSWAFGKFLWEWASARFSWLSLLVPFVQWFVGLSPTVWLSVIWMMWYW 201
GPSLYSILSPFLPLLPIFFCLWVYI                                           226
```

B (SEQ ID NO:3)

FIGURE 2

SEQUENCE LISTING

<160> NUMBER OF SEQ ID NOS: 5

<210> SEQ ID NO 1
<211> LENGTH: 27
<212> TYPE: PRT
<213> ORGANISM: Artificial
<220> FEATURE:
<223> OTHER INFORMATION: HBsAg "a" determinant
<220> FEATURE:
<221> NAME/KEY: MISC_FEATURE
<222> LOCATION: (2)..(2)
<223> OTHER INFORMATION: Xaa = Lys or Arg
<220> FEATURE:
<221> NAME/KEY: MISC_FEATURE
<222> LOCATION: (5)..(5)
<223> OTHER INFORMATION: Xaa = Thr or Met
<220> FEATURE:
<221> NAME/KEY: MISC_FEATURE
<222> LOCATION: (6)..(6)
<223> OTHER INFORMATION: Xaa = Ile or Thr
<220> FEATURE:
<221> NAME/KEY: MISC_FEATURE
<222> LOCATION: (7)..(7)
<223> OTHER INFORMATION: Xaa = Pro or Thr
<220> FEATURE:
<221> NAME/KEY: MISC_FEATURE
<222> LOCATION: (9)..(9)
<223> OTHER INFORMATION: Xaa = Gln or Arg
<220> FEATURE:
<221> NAME/KEY: MISC_FEATURE
<222> LOCATION: (11)..(11)
<223> OTHER INFORMATION: Xaa = Thr or Asn
<220> FEATURE:
<221> NAME/KEY: MISC_FEATURE
<222> LOCATION: (13)..(13)
<223> OTHER INFORMATION: Xaa = Met, Lys or Thr
<220> FEATURE:
<221> NAME/KEY: MISC_FEATURE
<222> LOCATION: (14)..(14)
<223> OTHER INFORMATION: Xaa = Phe, Ala, or Ser
<220> FEATURE:
<221> NAME/KEY: MISC_FEATURE
<222> LOCATION: (23)..(23)
<223> OTHER INFORMATION: Xaa = Ser or Leu
<220> FEATURE:
<221> NAME/KEY: MISC_FEATURE
<222> LOCATION: (25)..(25)
<223> OTHER INFORMATION: Xaa = Gly or Arg

<400> SEQUENCE: 1

Cys Xaa Thr Cys Xaa Xaa Xaa Ala Xaa Gly Xaa Ser Xaa Xaa Pro Ser
1 5 10 15

Cys Cys Cys Thr Lys Pro Xaa Asp Xaa Asn Cys
20 25

-continued

<210> SEQ ID NO 2
<211> LENGTH: 226
<212> TYPE: PRT
<213> ORGANISM: Artificial
<220> FEATURE:
<223> OTHER INFORMATION: amino acid sequence for the sAg wild-type adw antigen

<400> SEQUENCE: 2

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Ser Pro Val Cys
35 40 45

Leu Gly Gln Asn Ser Gln Ser Pro Thr Ser Asn His Ser Pro Thr Ser
50 55 60

Cys Pro Pro Ile Cys Pro Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Thr Thr Thr Thr Ser Thr Gly Pro Cys Lys Thr Cys Thr Thr Pro Ala
115 120 125

Gln Gly Asn Ser Met Phe Pro Ser Cys Cys Cys Thr Lys Pro Ser Asp
130 135 140

Gly Asn Cys Thr Cys Ile Pro Ile Pro Ser Ser Trp Ala Phe Ala Lys
145 150 155 160

Tyr Leu Trp Glu Trp Ala Ser Val Arg Phe Ser Trp Leu Ser Leu Leu
165 170 175

Val Pro Phe Val Gln Trp Phe Val Gly Leu Ser Pro Thr Val Trp Leu
180 185 190

Ser Ala Ile Trp Met Met Trp Tyr Trp Gly Pro Ser Leu Tyr Ser Ile
195 200 205

Val Ser Pro Phe Ile Pro Leu Leu Pro Ile Phe Phe Cys Leu Trp Val
210 215 220

Tyr Ile
225

<210> SEQ ID NO 3
<211> LENGTH: 226
<212> TYPE: PRT
<213> ORGANISM: Artificial
<220> FEATURE:
<223> OTHER INFORMATION: amino acid sequence for the sAg wild-type ayw antigen

<400> SEQUENCE: 3

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Asn Phe Leu Gly Gly Thr Thr Val Cys
35 40 45

Leu Gly Gln Asn Ser Gln Ser Pro Thr Ser Asn His Ser Pro Thr Ser
50 55 60

-continued

```
Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225


<210> SEQ ID NO 4
<211> LENGTH: 24
<212> TYPE: PRT
<213> ORGANISM: Artificial
<220> FEATURE:
<223> OTHER INFORMATION: adw wild-type "a" determinant

<400> SEQUENCE: 4

Cys Thr Thr Pro Ala Gln Gly Asn Ser Met Phe Pro Ser Cys Cys Cys
1               5                   10                  15

Thr Lys Pro Ser Asp Gly Asn Cys
            20


<210> SEQ ID NO 5
<211> LENGTH: 24
<212> TYPE: PRT
<213> ORGANISM: Artificial
<220> FEATURE:
<223> OTHER INFORMATION: ayw wild-type "a" determinant

<400> SEQUENCE: 5

Cys Met Thr Thr Ala Gln Gly Thr Ser Met Tyr Pro Ser Cys Cys Cys
1               5                   10                  15

Thr Lys Pro Ser Asp Gly Asn Cys
            20
```

RABBIT MONOCLONAL ANTIBODIES TO HEPATITIS B SURFACE ANTIGENS AND METHODS OF USING THE SAME

CROSS-REFERENCE TO RELATED APPLICATIONS

This application claims benefit under 35 U.S.C. § 119(e) of provisional application Ser. No. 60/577,561, filed on Jun. 7, 2004, and provisional application Ser. No. 60/583,734, filed on Jun. 28, 2004, which applications are incorporated herein by reference in their entireties.

TECHNICAL FIELD

The present invention pertains generally to hepatitis B virus (HBV). In particular, the invention relates to rabbit monoclonal antibodies directed against HBV surface antigens and methods of use thereof for diagnosis of HBV infection.

BACKGROUND

Hepatitis B virus (HBV) is a member of a group of small DNA-containing viruses that cause persistent noncytopathic infections of the liver. HBV infection in humans can cause severe jaundice, liver degeneration and death. HBV enters predominantly by the parenteral route, has a characteristic incubation period of 60 to 160 days, and may persist in the blood for years in chronic carriers. HBV is of great medical importance because it is one of the most common causes of chronic liver disease, such as hepatocellular carcinoma, in humans. Infected hepatocytes continually secrete viral particles that accumulate to high levels in the blood. Moreover, it is estimated that about 6 to 7% of the human population is infected, with the level of infection being as high as 20% of the population in certain regions of Southeast Asia and sub-Sahara Africa.

Several tests have been employed to detect the presence of HBV constituents in serum and other body fluids. These tests are primarily immunological in principle and depend on the presence of antibodies produced in humans or animals to detect specific viral proteins such as the hepatitis B surface antigen (HBsAg), hepatitis B core (nucleocapsid) antigen (HBcAg) or hepatitis B "E" antigen (HBeAg). However, there are increasing concerns about the contribution of variant HBsAgs relative to the production of false negatives in serological HBsAg diagnosis or blood screening assays.

In particular, HBV, due to its mode of replication by reverse transcription of its pre-genomic RNA, has a high rate of mutation relative to other DNA viruses. Amino acid substitutions have been described in all HBV DNA-encoded viral proteins such as polymerase, HBcAg and HBsAg. The group-specific "a" determinant region of HBV (amino acids 124-147, numbered relative to the S portion of HBsAg) has attracted the most attention, because mutations in this region have been found in 10-20% of vaccine escapees and have resulted in the misdiagnoses of variant HBVs, even using the most current serological assays on the market. Thus, there is a need for the development of reliable diagnostic tests to detect HBV in viremic samples, in order to prevent transmission of the virus through blood and plasma derivatives or by close personal contact.

Rabbit-rabbit and rabbit-mouse hybridomas have been used in an attempt to generate monoclonal antibodies with increased immunoreactivity. See, e.g., U.S. Pat. Nos. 4,977,081; 4,859,595; 5,472,868; 5,675,063; Spieker-Polet et al., *Proc. Natl. Acad. Sci. USA* (1995) 92:9348-9352. Rabbit monoclonal antibodies are desirable for several reasons. First, rabbits may recognize antigens and epitopes that are not immunogenic in mice or rats, the two species from which monoclonal antibodies are usually generated. Additionally, rabbit antibodies are generally of high affinity. U.S. Pat. No. 4,859,595 describes the production of rabbit monoclonal antibodies to HBsAg using rabbit-rabbit fusions.

However, there remains a need for improved immunoassays using monoclonal antibodies with broader immunoreactivity against the various HBsAg mutants. The wide-spread availability of reagents for use in an accurate and efficient assay for HBV infection would be highly desirable.

SUMMARY OF THE INVENTION

The present invention provides highly immunoreactive monoclonal antibodies for the simple, accurate and efficient diagnosis of HBV infection. The antibodies are produced from rabbit hybridomas and are immunoreactive against various mutant HBV strains. Thus, assay methods using the rabbit monoclonal antibodies are more accurate and the number of false negatives seen with other serological tests is reduced. Assays using the antibodies therefore allow the detection of HBV infection caused by a variety of HBV mutants and, if infection is detected, the individual can be given appropriate treatment in adequate time to help prevent liver damage and death.

Accordingly, in one embodiment, the invention is directed to an anti-HBV rabbit monoclonal antibody that recognizes an HBsAg mutant with a mutation in the "a" determinant region, or an immunoreactive fragment thereof, such as a Fab, $F(ab')_2$, Fv or an sFv fragment. In certain embodiments, the antibody recognizes more than one HBsAg mutant with a mutation in the "a" determinant region. In additional embodiments, the antibody also recognizes a wild-type HBsAg. In yet further embodiments, the HBsAg mutant is a mutant sAg, such as a mutant that comprises the sequence of the "a" determinant region of F134A, F134S, G145R, S143L, P142S or Q129R/M133T. In further embodiments, the antibody recognizes an HBsAg and/or one or at least two mutant HBSAg selected from the group consisting of F134A, F134S, G145R, S143L, P142S and Q129R/M133T. Any of the antibodies above can be produced using a rabbit-rabbit hybridoma or a rabbit-mouse hybridoma.

In additional embodiments, the invention is directed to hybridomas 99S6 (ATCC Accession number PTA-6015) and 99S9 (ATCC Accession number PTA-6014), and antibodies produced by these hybridomas. In further embodiments, the invention is directed to a rabbit monoclonal antibody that recognizes the same epitope as an antibody produced by hybridoma 99S6 and/or 99S9.

In further embodiments, the invention is directed to a method of detecting HBV surface antigens in a biological sample. The method comprises:

contacting the biological sample with at least one rabbit monoclonal antibody according to any of the embodiments above, under conditions which allow HBV antigens, when present in the biological sample, to bind to the antibody to form an antibody/antigen complex; and detecting the presence or absence of the antibody/antigen complex, thereby detecting the presence or absence of HBV surface antigens in the sample.

In preferred embodiments of the above method, the at least one rabbit monoclonal antibody is the antibody produced by the hybridoma 99S6 or the hybridoma 99S9. In certain embodiments, the at least one rabbit monoclonal antibody is detectably labeled. In certain embodiments, the method further comprises reacting the biological sample with one or more additional antibodies directed against a wild-type HBsAg or an HBsAg mutant with a mutation in the "a" determinant region. The one or more additional antibodies may comprise an additional monoclonal antibody, such as a mouse monoclonal antibody.

In additional embodiments, the invention is directed to an immunodiagnostic test kit for detecting HBV infection. The test kit comprises:

at least one rabbit monoclonal antibody, or immunoreactive fragment thereof according to any of the embodiments above; and instructions for conducting the immunodiagnostic test.

In preferred embodiments of the above method, the at least one rabbit monoclonal antibody is the antibody produced by the hybridoma 99S6 or the hybridoma 99S9. In certain embodiments, the test kit further comprises one or more additional antibodies directed against a wild-type HBsAg or an HBsAg mutant with a mutation in the "a" determinant region. The one or more additional antibodies may comprise an additional monoclonal antibody, such as a mouse monoclonal antibody.

In further embodiments, the invention is directed to a solid support comprising at least one rabbit monoclonal antibody or immunoreactive fragment thereof according to any of the above embodiments. In preferred embodiments of the solid support, the at least one rabbit monoclonal antibody is the antibody produced by the hybridoma 99S6 or the hybridoma 99S9. In certain embodiments, the support further comprises one or more additional antibodies directed against a wild-type HBsAg or an HBsAg mutant with a mutation in the "a" determinant region. The one or more additional antibodies may comprise an additional monoclonal antibody, such as a mouse monoclonal antibody. In additional embodiments, the solid support further comprises at least two internal controls, wherein one of the controls defines the lower detection limit for a positive result in an immunoassay using the solid support and the other control defines a highly positive result in an immunoassay using the solid support. In some embodiments, the solid support is a nitrocellulose strip.

In yet additional embodiments, the invention is directed to an immunodiagnostic test kit for detecting HBV. The test kit comprises:

(a) a solid support according to any of the above embodiments; and (b) instructions for conducting the immunodiagnostic test.

In a further embodiment, the invention is directed to a method of detecting the presence of HBV surface antigens in a biological sample. The method comprises:

(a) providing a biological sample;

(b) providing a solid support as described above;

(c) contacting the biological sample with the solid support, under conditions which allow HBV surface antigens, if present in the biological sample, to bind with at least one of the rabbit monoclonal antibodies to form an antibody/antigen complex; and (d) detecting the presence of the antibody/antigen complex, thereby detecting the presence of HBV surface antigens in the biological sample.

In certain embodiments, the method further comprises:

(e) removing unbound HBV antigens;

(f) providing one or more moieties capable of associating with the antibody/antigen complex; and (g) detecting the presence of the one or more moieties, thereby detecting the presence of HBV surface antigens in the biological sample.

In additional embodiments of the method, the one or more moieties comprises a detectably labeled HBV antibody, such as a detectably labeled rabbit monoclonal antibody that recognizes an HBsAg mutant with a mutation in the "a" determinant region, or an immunoreactive fragment thereof. The detectable label can be an enzyme. Additionally, the biological sample can be from a human blood sample.

In further embodiments, the invention is directed to a method of detecting the presence of anti-HBsAg antibodies in a biological sample. The method comprises:

(a) providing a solid support as described above;

(b) contacting the solid support with one or more HBsAgs, under conditions which allow the one or more HBsAgs to bind with at least one of the rabbit monoclonal antibodies to form an antibody/antigen complex;

(d) contacting the solid support having the antibody/antigen complex with a biological sample, under conditions which allow anti-HBsAg antibodies, if present in the biological sample, to bind with the antibody/antigen complex to form an antibody/antigen/antibody complex; and (e) detecting the presence of the antibody/antigen/antibody complex, thereby detecting the presence of anti-HBsAg antibodies in the biological sample.

In further embodiments, the method further comprises:

(f) removing unbound antibodies;

(g) providing one or more moieties capable of associating with the antibody/antigen/antibody complex, such as one or more moieties comprising a detectably labeled immunoglobulin molecule; and (h) detecting the presence of the one or more moieties, thereby detecting the presence of anti-HBsAg antibodies in the biological sample.

In additional embodiments, the invention is directed to a method of preparing a blood supply comprising whole blood, platelets, plasma or serum, substantially free of HBV. The method comprises:

(a) screening aliquots of whole blood, platelets, plasma or serum from collected blood samples by a method above;

(b) eliminating any samples in which an HBV antigen is detected; and (c) combining samples in which no HBV antigen is detected to provide a blood supply substantially free of HBV.

In further embodiments, the invention is directed to a method of preparing a blood supply comprising whole blood, platelets, plasma or serum, substantially free of HBV. The method comprises:

(a) screening aliquots of whole blood, platelets, plasma or serum from collected blood samples by a method above;

(b) eliminating any samples in which an anti-HBsAg antibody is detected; and (c) combining samples in which no anti-HBsAg antibody is detected to provide a blood supply substantially free of HBV.

In yet additional embodiments, the invention is directed to a method of screening a donated tissue or organ prior to transplantation to provide a tissue or organ substantially free of HBV. The method comprises:

(a) screening a sample from the tissue or organ by a method above;

(b) eliminating a tissue or organ in which an HBV antigen is detected to provide a tissue or organ substantially free of HBV.

In further embodiments, the invention is directed to a method of screening a donated tissue or organ prior to transplantation to provide a tissue or organ substantially free of HBV. The method comprises:

(a) screening a sample from the tissue or organ by a method above;

(b) eliminating a tissue or organ in which an anti-HBsAg antibody is detected to provide a tissue or organ substantially free of HBV.

In still further embodiments, the invention is directed to a method of preparing an anti-HBV rabbit monoclonal antibody. The method comprises:

(a) immunizing a rabbit with an HBsAg mutant with a mutation in the "a" determinant region;

(b) fusing cells that produce antibodies against the HBsAg mutant from the rabbit with a cell from an immortalized cell line to produce a hybridoma;

(c) selecting for the hybridoma;

(d) culturing the selected hybridoma; and (e) collecting the antibody secreted by the cultured hybridoma.

In certain embodiments, the immunizing step comprises immunizing a rabbit with more than one HBsAg mutant. In certain embodiments, the antibody-producing cells are rabbit splenocytes. The splenocytes can be fused with a cell from an immortalized rabbit cell line, such as a rabbit plasmacytoma, to produce a rabbit-rabbit hybridoma, or with a cell from an immortalized mouse cell line, to produce a rabbit-mouse hybridoma.

In certain embodiments, of the method above, the HBsAg mutant is a mutant sAg, such as a mutant that comprises the sequence of the "a" determinant region of F134A, F134S, G145R, S143L, P142S or Q129R/M133T. In other embodiments, the HBsAg mutant comprises F134A, F134S, G145R, S143L, P142S or Q129R/M133T. In yet further embodiments, the rabbit is immunized with at least two HBsAg mutants with different mutations in the "a" determinant region, such as with at least two HBsAg mutants selected from the group consisting of F134A, F134S, G145R, S143L, P142S or Q129R/M133T. In additional embodiments, the rabbit is immunized with HBsAg mutants F134A, F134S, G145R, S143L, P142S and Q129R/M133T. In further embodiments, the rabbit is additionally immunized with a wild type HBsAg.

In additional embodiments, the invention is directed to an anti-HBV rabbit monoclonal antibody produced by the methods above.

In yet further embodiments, the invention is directed to a method of preparing a rabbit-rabbit hybridoma. The method comprises:

(a) immunizing a rabbit with an HBsAg mutant with a mutation in the "a" determinant region;

(b) fusing splenocytes that produce antibodies against the HBsAg mutant from the rabbit with cells from a rabbit plasmacytoma;

(c) selecting for cells that secrete the antibodies.

In additional embodiments, the invention is directed to a polynucleotide encoding a rabbit monoclonal antibody or an immunoreactive fragment thereof such as a Fab, $F(ab')_2$, Fv or an sFv fragment, as described above.

These and other embodiments of the subject invention will readily occur to those of skill in the art in view of the disclosure herein.

BRIEF DESCRIPTION OF THE FIGURES

FIG. 1 shows a schematic of the HBV surface antigen depicting the highly conformational structure of the protein (lower panel, solid line) and the amino acid sequence (SEQ ID NO:1) around the "a" determinant (from aa 121-147, upper panel, in circles). The arrows indicate the position and substitution of various known HBsAg variants.

FIGS. 2A and 2B (SEQ ID NOS:2 and 3) show the amino acid sequence for the sAg wild-type adw and ayw antigens, respectively.

DETAILED DESCRIPTION OF THE INVENTION

Figure 3A:
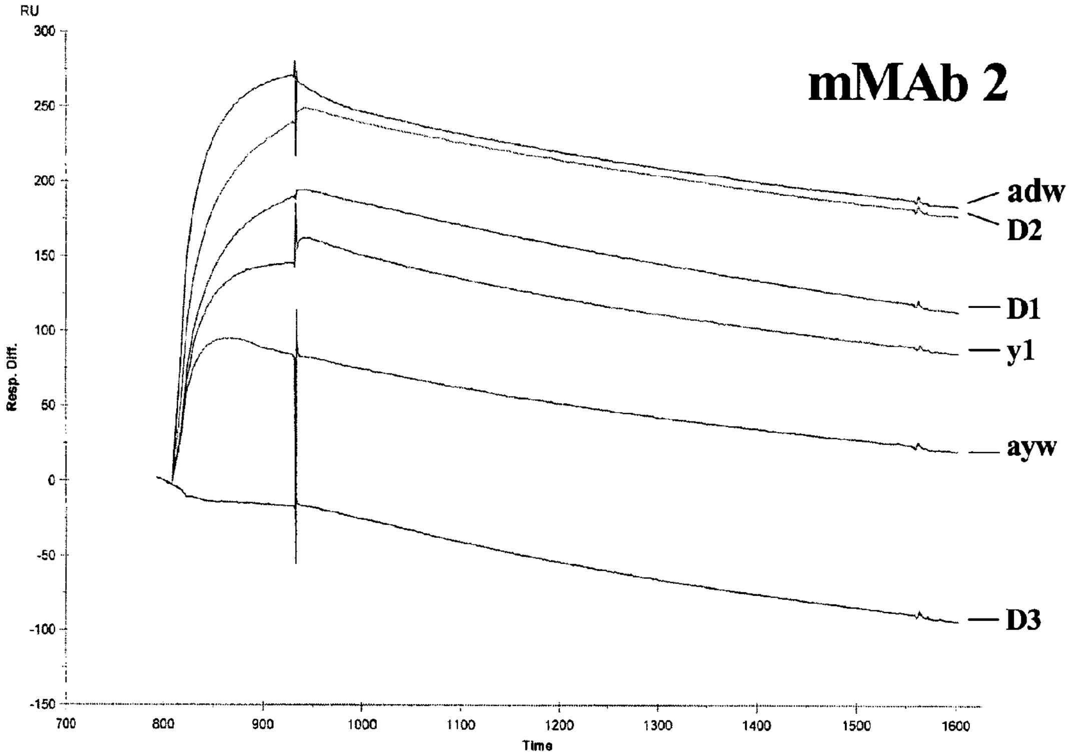
FIGS. 3A-3D show the immunoreactivities of rabbit monoclonal antibodies from 99S6 (FIG. 3B) and 99S9 (FIG. 3D), in comparison with the mouse antibodies mMAb1 (FIG. 3C) and mMAb2 (FIG. 3A) against the HBV mutant panel described above.
Figure 3B:
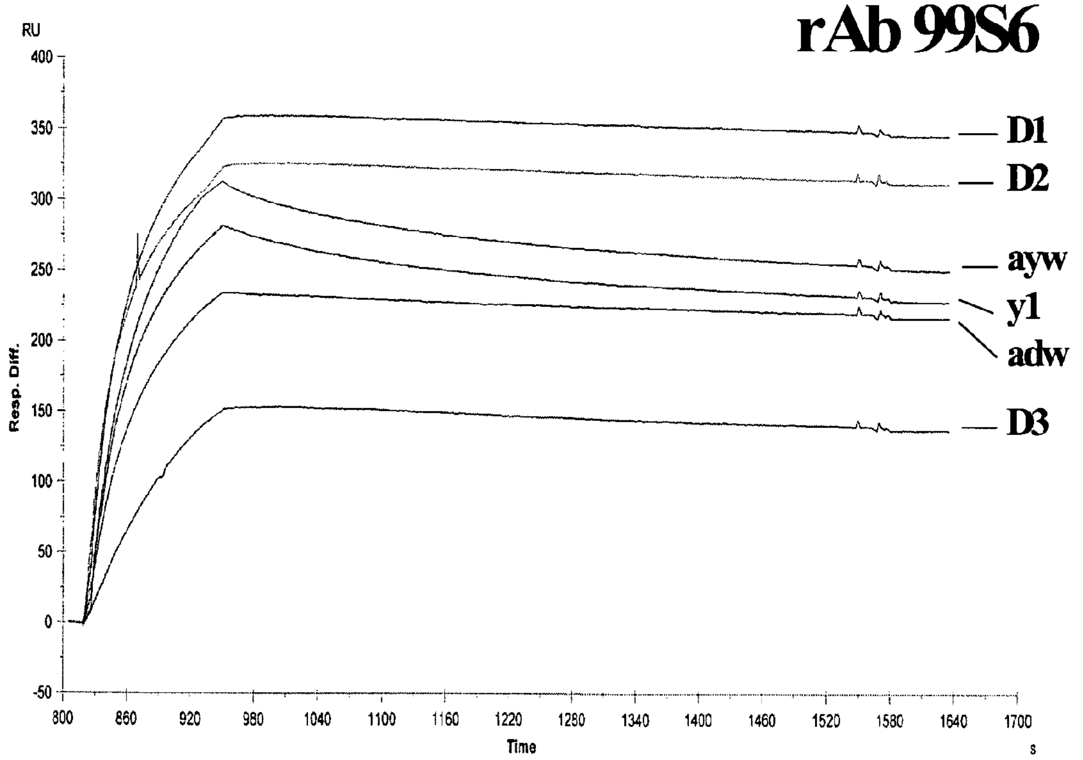
Figure 3C:
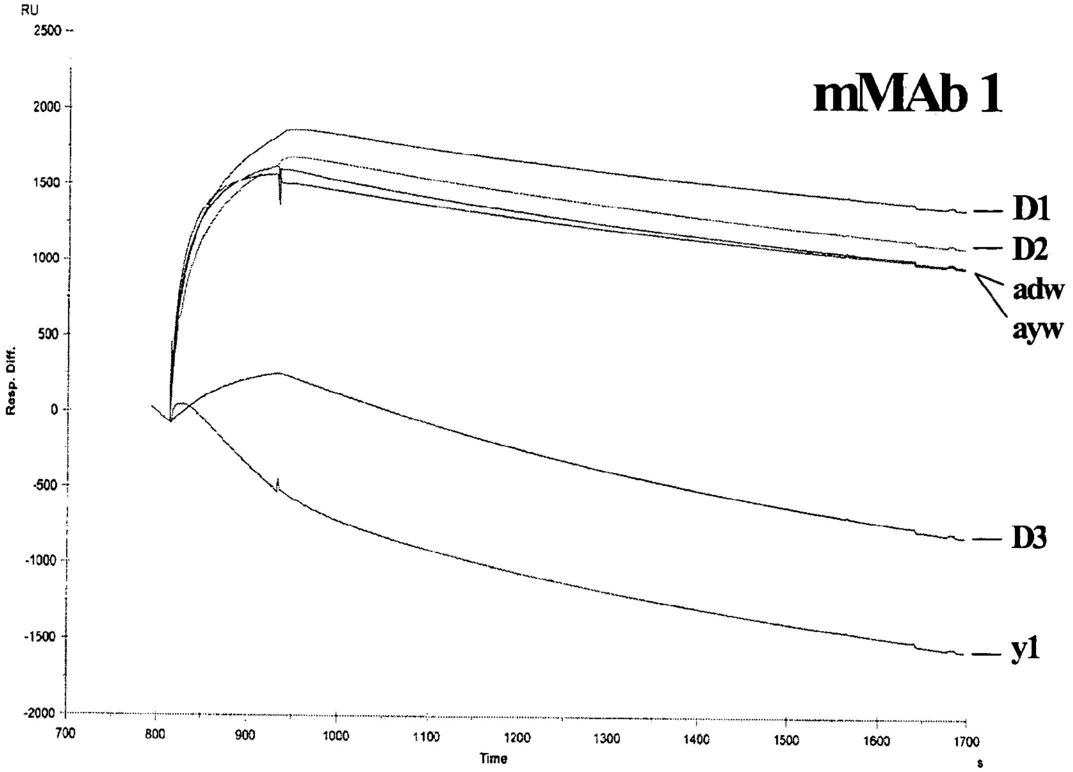
Figure 3D:
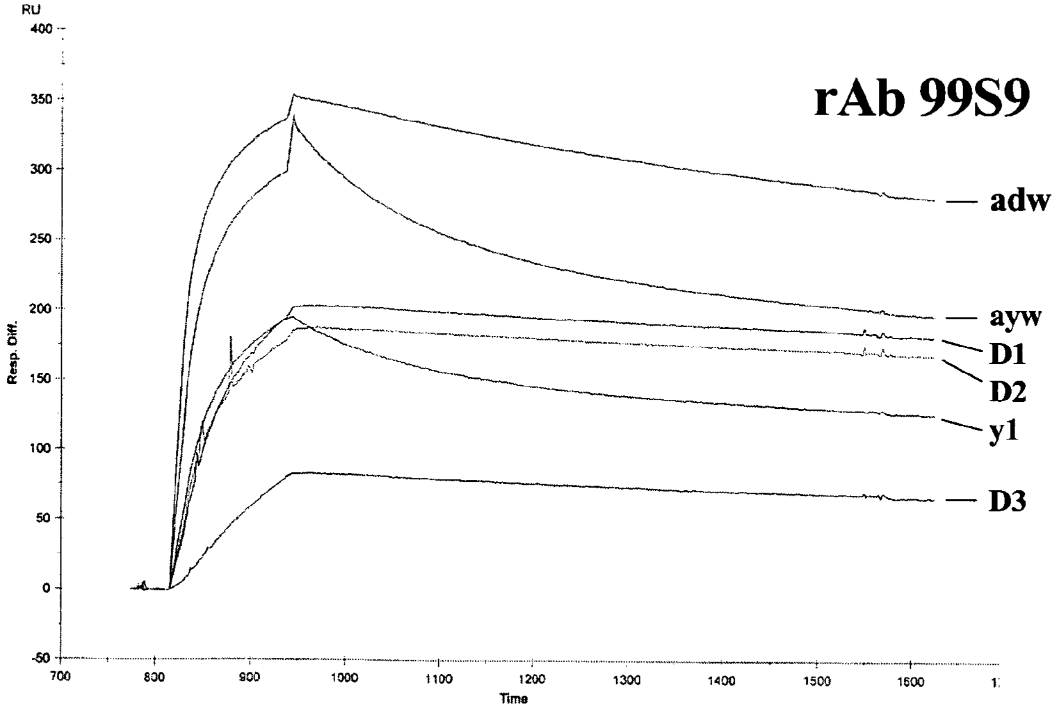

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology,* 3rd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a rabbit monoclonal antibody" includes a mixture of two or more such polypeptides, and the like.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The term "antigen" refers to a polypeptide, whether native, recombinant or synthetic, which includes one or more epitopes that recognize an antibody. The antigen in question need not include the full-length amino acid sequence of the reference molecule but can include only so much of the molecule as necessary in order to generate an immunological reaction (i.e., when the antigen is used for generating antibodies) or to react with the HBV antibody of interest (i.e., where the antigen is being detected in an assay). Thus, only one or few epitopes of the reference molecule need be present. Furthermore, the antigen may comprise a fusion protein between the full-length reference molecule or a fragment of the reference molecule, and another protein such as another HBV antigen and/or a protein that does not disrupt the reactivity of the HBV antigen. It is readily apparent that the antigen may therefore comprise the full-length sequence, fragments, truncated and partial sequences, as well as analogs, muteins and precursor forms of the reference molecule. The term also intends deletions, additions and substitutions to the reference sequence, so long as the antigen retains the ability to stimulate antibody production and/or to react with HBV antibodies.

In this regard, natural variation will occur from isolate to isolate within a particular HBV strain. Thus, the term is intended to encompass such variation and, in particular, an antigen that varies in its amino acid composition by not more than about 20 number percent, more preferably by not more than about 10 to 15 number percent, and most preferably, by not more than about 5 number percent, from the reference antigen. Proteins having substantially the same amino acid sequence as the reference molecule, but possessing minor amino acid substitutions that do not substantially affect the antibody binding capabilities of the antigen, are therefore within the definition of the reference polypeptide.

An antigen "derived from" an HBV strain or isolate intends an antigen which comprises a sequence of one or more regions or portions of regions of an antigen encoded by the reference HBV genome. Typically, the antigen is composed of regions or portions of regions that include epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

The terms "analog" and "mutein" refer to biologically active derivatives of the reference molecule, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity and which are "substantially homologous" to the reference molecule as defined below. A number of conserved and variable regions are known between the various isolates and, in general, the amino acid sequences of epitopes derived from these regions will have a high degree of sequence homology, e.g., amino acid sequence homology of more than 50%, generally more than 60%-70%, when the two sequences are aligned. The term "mutein" refers to peptides having one or more peptide mimics (e.g., "peptoids"). Preferably, the analog or mutein has at least the same immunoreactivity as the native molecule. Methods for making polypeptide analogs and muteins are known in the art and are described further below.

The terms "analog" and "mutein" also encompass purposeful mutations that are made to the reference molecule. Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the antigen of interest may include up to about 5-10 conservative or non-conservative amino acid substitutions, or even up to about 15-25, 50 or 75 conservative or non-conservative amino acid substitutions, or any integer between 5-75, so long as the desired function of the molecule remains intact. One of skill in the art can readily determine regions of the molecule of interest that can tolerate change by reference to Hopp/Woods and Kyte-Doolittle plots, well known in the art.

By "antigen fragment" is intended an antigen consisting of only a part of the intact full-length antigen polypeptide sequence and structure. The fragment can include a C-terminal deletion, an N-terminal deletion, and/or an internal deletion of the native polypeptide. By "immunogenic fragment" is meant a fragment of a polypeptide that includes one or more epitopes and thus elicits one or more of the immunological responses described herein. An "immunogenic fragment" of a particular HBV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

By "HBsAg" is meant an HBV surface antigen derived from any of the various HBV strains and isolates. The term intends surface antigens which include a substantially complete S domain of an HBsAg polypeptide (termed "sAg" herein), as well as immunogenic fragments thereof. An S domain of HBsAg is "substantially complete" if it contains the native sequence of the polypeptide with or without minor deletions of one or a few amino acids from either the N-terminal or C-terminal regions or within the polypeptide. For example the HBsAg S domain can be truncated by a few amino acids, i.e., up to about 3, 5, 7, or 10 amino acids, without greatly affecting its antigenicity. An HBsAg antigen for use herein will generally include a region corresponding to the "a" determinant, found at amino acid positions 124-147, numbered relative to the sAg. This region is described further below. The term also intends an antigen that includes the preS2 (formerly called preS) domain in addition to the S domain, or both the preS2 and preS1 domains of HBsAg, in addition to the S domain. Valenzuela, et al. (1982) *Nature* 298:347-350, describes the gene for a representative HBsAg. See, also, Valenzuela, et al. (1979) *Nature* 280:815-819.

A "mutant" HBsAg molecule, as used herein, refers to analogs of wild-type HBsAgs, as defined above. For the purpose of this invention, by "wild-type HBsAgs" is meant HBsAgs from the ayw and adw subtypes. These analogs may arise by natural mutational events, e.g., in the case of escape mutants, or may be purposefully created. Representative mutant HBsAg sequences are shown in FIG. 1 herein. Additional naturally occurring mutants are known in the art and the nucleotide sequences and corresponding amino acid sequences for surface antigens from these mutants have been deposited with GenBank. See, e.g., NCBI accession numbers AY341335 (naturally occurring surface mutant with multiple mutations in the "a" determinant of sAg), X59795 (naturally occurring mutant from the ayw subtype); AF01360 and AF013629 (naturally occurring mutants from the adw subtype) and Zuckerman et al. 1999 (J. Med Virol. 58:193).

By "immunogenic" sequence of an HBsAg is meant an HBsAg molecule that includes an amino acid sequence with at least one epitope such that the molecule is capable of stimulating the production of antibodies in an appropriate host. By "epitope" is meant a site on an antigen to which specific B cells and/or T cells respond, rendering the HBV epitope in question capable of stimulating antibody production. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids or more.

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

An "immunogenic composition" is a composition that comprises at least one immunogenic polypeptide (e.g., an HBsAg antigen or antibody).

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different isolates or strains of HBV which antigenic determinants are not necessarily identical due to sequence variation, but which occur in equivalent positions in the HBV sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

An "antibody" intends a molecule that "recognizes," i.e., specifically binds to an epitope of interest present in an antigen. By "specifically binds" is meant that the antibody interacts with the epitope in a "lock and key" type of interaction to form a complex between the antigen and antibody, as opposed to non-specific binding that might occur between the antibody and, for instance, components in a mixture that includes the test substance with which the antibody is reacted. Thus, an anti-HBV antibody is a molecule that specifically binds to an epitope of an HBV protein. The term "antibody" as used herein includes antibodies obtained from both polyclonal and monoclonal preparations, as well as, the following: hybrid (chimeric) antibody molecules (see, for example, Winter et al., *Nature* (1991) 349:293-299; and U.S. Pat. No. 4,816,567); F(ab')2 and F(ab) fragments; Fv molecules (non-covalent heterodimers, see, for example, Inbar et al., *Proc Natl Acad Sci USA* (1972) 69:2659-2662; and Ehrlich et al., *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs; minibodies (see, e.g., Pack et al., *Biochem* (1992) 31:1579-1584; Cumber et al., *J Immunology* (1992) 149B:120-126); humanized antibody molecules (see, for example, Riechmann et al., *Nature* (1988) 332:323-327; Verhoeyan et al., *Science* (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

As used herein, the term "rabbit monoclonal antibody" refers to a monoclonal antibody, as defined above, produced by immunizing a rabbit with an antigen of interest (e.g., a mutant HBsAg). A "rabbit monoclonal antibody" can be produced using rabbit-rabbit hybridomas (i.e., fusions between an antibody-producing cell from the immunized rabbit with an immortalized cell from a rabbit), rabbit-mouse hybridomas (i.e., fusions between an antibody-producing cell from the immunized rabbit with an immortalized cell from a mouse), and the like, described more fully below.

A "mouse monoclonal antibody" refers to a monoclonal antibody, as defined above, produced by immunizing a mouse, with an antigen of interest (e.g., a mutant HBsAg). A "mouse monoclonal antibody" is produced using conventional methods well known in the art, from mouse-mouse hybridomas, described more fully below.

As used herein, a "solid support" refers to a solid surface to which a macromolecule, e.g., an antibody, protein, polypeptide, peptide, polynucleotide can be attached, such as a magnetic bead, latex bead, microtiter plate well, glass plate, nylon, agarose, polyacrylamide, silica particle, nitrocellulose membrane, and the like.

"Immunologically reactive" means that the antibody in question will react specifically with HBV antigens present in a biological sample from an HBV-infected individual.

An "immunoreactive fragment" of an antibody, is a molecule consisting of only a portion of the intact antibody sequence and structure, and that is immunologically reactive as defined above. Non-limiting examples of such immunoreactive fragments include $F(ab')_2$, Fv, and sFv molecules, that are capable of exhibiting immunological binding properties of the parent antibody molecule from which they are derived.

"Immune complex" intends the combination formed when an antibody binds to an epitope on an antigen.

As used herein, a "biological sample" refers to a sample of tissue or fluid isolated from a subject such as, but not limited to, blood, plasma, platelets, serum, fecal matter, urine, bone marrow, bile, spinal fluid, lymph fluid, cerebrospinal fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

As used herein, the terms "label" and "detectable label" refer to a molecule capable of detection, including, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that novel rabbit monoclonal antibodies, directed against mutant HBsAgs, are far more immunoreactive in assays for detecting HBV infection than conventional mouse monoclonal antibodies. The rabbit monoclonal antibodies of the present invention are reactive with a broader range of HBsAg mutants than conventional mouse monoclonal antibodies. Moreover, the rabbit monoclonal antibodies of the present invention are typically also reactive with wild-type HBsAgs. Indeed, a single rabbit monoclonal antibody according to the present invention is as effective as the use of multiple mouse monoclonal antibodies for detecting the presence of HBV antigens, which can be indicative of HBV infection. Thus, the rabbit monoclonal antibodies of the present invention decrease the number of false negatives obtained with assays using, e.g., mouse monoclonal antibodies and are therefore useful in diagnostic methods for accurately detecting HBV infection. The assays of the present invention can also utilize additional antibodies, such as additional mouse monoclonal antibodies, to provide the ability to diagnose HBV infection from a wide variety of isolates and escape mutants.

The methods are useful for detecting HBV infection in humans, as well as for detecting HBV infection in blood samples, including without limitation, in whole blood, serum, platelets, and plasma, as well as in tissues and organs for transplantation, in particular by detecting the presence of HBV antigens or HBV antibodies. Thus, the methods can be used to diagnose HBV infection in a subject, such as a human subject, as well as to detect HBV contamination in donated blood samples. Aliquots from individual donated samples or pooled samples can be screened for the presence of HBV and those samples or pooled samples contaminated with HBV can be eliminated before they are combined. In this way, a blood supply substantially free of HBV contamination can be provided. Similarly, samples from tissues and organs to be used in transplantation can also be screened in order to eliminate contaminated specimens.

In order to further an understanding of the invention, a more detailed discussion is provided below regarding HBV antigens, antibodies and diagnostic methods for use with the subject invention.

HBV Surface Antigens

The hepatitis B surface antigens are made up of three size classes of proteins that share carboxy-terminal sequences. These proteins include large (L, the preS2 domain), medium (M, the preS1 domain), and small (S, the sAg domain). All three proteins are found in infectious virions (often referred to as Dane particles) recovered as 42 nm spheres from the serum of infected patients. Serum samples also contain empty spherical particles averaging 22 nm, which contain primarily the S class of proteins (sAg). Mammalian cell lines transfected exclusively with DNA encoding the sAg protein release 20 nm empty spheres similar to those from infected cells. Moreover, yeast cells transformed with the same gene form analogous spheres, which are found to be equally immunogenic as the 22 nm spheres from infected cells. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, 5,965,140, incorporated herein by reference in their entireties, Beames et al., *J. Virol.* (1995) 69:6833-6838, Birnbaum et al., *J. Virol.* (1990) 64:3319-3330, Zhou et al., *J. Virol.* (1991) 65:5457-5464, for descriptions of the recombinant production of various HBV particles.

Thus, as explained above, HBsAgs for use in producing the rabbit monoclonal antibodies of the present invention can include immunogenic regions of sAg, preS1 and/or preS2, as well as immunogenic regions from any combination of the above, such as sAg/preS1, sAg/preS2, and sAg/preS1/preS2. Optionally, an HBsAg polypeptide can comprise more than one sAg, preS1, or preS2 polypeptide. Additionally, the sAg, preS1, and preS2 polypeptides may be derived from the same or different isolates of HBV. These polypeptides may also be provided as a fusion protein or as separate polypeptides. The sequences of HBsAgs from hundreds of different HBV isolates are known and can be readily obtained from the NCBI database.

A preferred HBsAg for use in the invention comprises at least the sequence of amino acids of the "a" determinant region of HBV (amino acids 124-147, numbered relative to the sAg). Representative wild-type sequences for this region are CTTPAQGNSMFPSCCCTKPSDGNC (SEQ ID NO:4, adw wild-type); and CMTTAQGTSMYPSCCCTKPSDGNC (SEQ ID NO:5, ayw wild-type). Mutations in this region of sAg have been found in a large number of HBV vaccine escapees. For descriptions of a number of HBsAg variants, see, Ashton-Richardt P G, Murray K. (1989) Mutants of the hepatitis B virus surface antigen and define some antigenically essential residues in the immunodominant "a" region. J. Medical Virology 29: 196-203; Norder H. Courouce A_M, Magnius L (1992) Molecular basis of hepatitis B virus serotype variation within the four major subtype. J. General Virology 73: 3141-3145; Carman W F, Zanetti A R, et. al. (1990) Vaccine-induced escape mutant of hepatitis B virus. Lancet 336: 325-329; Fujii H. Moriyama K. et al. Gly 145 to Arg substitution in HBs antigen of immune escape mutant of hepatitis B virus. Biochem. Biophys Res Comm 184: 1152-1157; Carman, W. Vaccine-associated mutants of hepatitis B virus. Viral Hepatitis and Liver Disease (1945) pp: 243-247, Eds: K. Nishioka, H. Suzuki, S. Mishiro T. Oda)

Thus, HBsAgs including mutations in this region are particularly useful herein. Representative mutants for this region include F134A, F134S, G145R, S143L, P142S and Q129R/

M133T. In each of the mutant designations, the number indicates the position of the substituted amino acid, the letter before the number indicates the amino acid at that position in the WT sequence and the letter following the number indicates the amino acid at that position in the mutant. These mutants are merely representative and it is to be understood that a large number of additional naturally occurring mutants exist, which mutants will find use with the present invention. Additionally, synthetic mutants with mutations in the "a" determinant region will also find use herein. Variants having mutations in regions other than the "a" determinant region, as defined above, may also find use in the present invention. For example, the variant having a substitution of Q for P at amino acid position 120 (P120Q), finds use as antigen for generating monoclonal antibodies.

Antigens for use with the present invention can be obtained using standard techniques. The HBV antigens are conveniently generated using recombinant methods, well known in the art. See, e.g., U.S. Pat. Nos. 4,722,840, 5,098,704, 5,324,513, 5,965,140 and 6,306,625, for descriptions of the recombinant production of HBV antigens, all of which are incorporated herein by reference in their entireties. For example, the HBsAg S protein coding sequence can be isolated by phenol extraction of DNA from Dane particles present in infected human serum, using methods known in the art, such as described in U.S. Pat. No. 4,710,463, the disclosure of which is incorporated herein by reference in its entirety. The isolated DNA can then be digested with a restriction endonuclease. The choice of endonuclease will depend, in part, on the particular Dane particles. For example, the HBsAg coding sequence of HBV DNA of certain Dane particles of the adw serotype can be isolated as a single BamHI fragment; the HBsAg coding sequence of HBV DNA of certain Dane particles of the ayw serotype can be isolated as a HhaI fragment. HBV DNA of Dane particles of the same serotype may also exhibit different patterns of restriction sites.

Oligonucleotide probes can be devised based on the known sequences of the HBV genome and used to probe genomic or cDNA libraries for HBV genes encoding for the antigens useful in the present invention. The genes can then be further isolated using standard techniques and, if desired, restriction enzymes employed to mutate the gene at desired portions of the full-length sequence. See, e.g., Sambrook et al., supra, for a description of techniques used to obtain and isolate DNA.

Finally, the genes encoding the HBV antigens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Polynucleotides can comprise coding sequences for the various polypeptides which occur naturally or can include artificial sequences which do not occur in nature. These polynucleotides can be ligated to form a coding sequence for a fusion protein, if desired, using standard molecular biology techniques.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

If present, the signal sequence can be the native leader found in association with the HBV antigen of interest. Alternatively, a heterologous signal sequence can be present which can increase the efficiency of secretion. A number of representative leader sequences are known in the art and include, without limitation, the yeast $\alpha$-factor leader, the TPA signal peptide, the Ig signal peptide, and the like. Sequences for these and other leader sequences are well known in the art.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

Any suitable expression vector can be constructed or utilized to express any form of HBsAg of the invention. An exemplary vector is pCMVII, a pUC19-based cloning vector designed for expression in mammalian cells. pCMVII comprises the following elements: human CMV IE enhancer/promoter, human CMV intron A, a human tissue plasminogen activator (tPA) leader, a bovine growth hormone poly A terminator (BGHt), a ColE1 origin of replication, and an Amp R ampicillin resistance gene. For example, pCMVII-pS2-sAg can be used for expression of preS2-sAg. In this vector, the coding sequences for the sAg and preS2 domains of HBsAg have been inserted into pCMVII between CMV intron A and BGHt. This vector can also be modified by, e.g., removing the preS2 domain or adding the coding sequence for the preS1 domain. These vectors are provided by way of example and are not intended to limit the scope of the invention. The above vectors are described in detail in U.S. Pat. No. 6,740,323, incorporated herein by reference in its entirety.

As explained above, it may also be desirable to produce mutants or analogs of the polypeptide of interest. Mutants or analogs of HBV polypeptides for use in the subject compositions may be prepared by the deletion of a portion of the sequence encoding the molecule of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The HBV antigens can also be synthesized using chemical polymer syntheses such as solid phase peptide synthesis. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques.

The HBV antigens, obtained as described above, are then used to produce rabbit monoclonal antibodies for use in diagnostics.

Anti-HBV Antibodies

The HBV antigens can be used to produce HBV-specific polyclonal and monoclonal antibodies for use in diagnostic and detection assays. HBV-specific polyclonal and monoclonal antibodies specifically bind to HBV antigens. In particular, the HBV antigens can be used to produce polyclonal antibodies by administering the HBV antigen to a mammal, such as a mouse, a rat, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Rabbit and mouse monoclonal antibodies directed against HBV-specific epitopes present in the proteins can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2-6 weeks later with one or more injections of the antigen in saline, preferably using Freund's incomplete adjuvant ("FIA"). In one embodiment, the animal is immunized with one or more HBsAg mutants, preferably a mixture of 2 to 5 different HBsAg mutants is used. Wild-type HBsAgs may also be included in the immunogen. In a preferred regime, the animal, preferably a rabbit, is initially immunized with a wild type HBsAg, and thereafter boosted with one or more HBsAg mutants. Particularly useful as immunogen are HBsAg mutants which have been found to occur naturally, e.g., D3, D2, D1, Y1, Y2, described further below. Antibodies may also be generated by in vitro immunization, using methods known in the art. See, e.g., James et al., *J. Immunol. Meth.* (1987) 100:5-40.

Polyclonal antisera is then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* (1995) 92:9348-9352 and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from the ATCC.

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* (2001) 20:189-198. The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing HBV-specific antibodies can be identified using RIA or ELISA and isolated by cloning in semi-solid agar or by limiting dilution. Clones producing HBV-specific antibodies can isolated by another round of screening.

An alternative technique for generating the rabbit monoclonal antibodies of the present invention is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* (1996) 93:7843-7848, for a description of this method.

For further descriptions of rabbit monoclonal antibodies and methods of making the same from rabbit-rabbit and rabbit-mouse fusions, see, e.g., U.S. Pat. Nos. 5,675,063 (rabbit-rabbit); 4,859,595 (rabbit-rabbit); 5,472,868 (rabbit-mouse); and 4,977,081 (rabbit-mouse). For a description of the production of conventional mouse monoclonal antibodies, see, e.g., Kohler and Milstein, *Nature* (1975) 256:495-497.

It may be desirable to provide chimeric antibodies. Chimeric antibodies composed of human and non-human amino acid sequences may be formed from the monoclonal antibody molecules described above to reduce their immunogenicity in humans (Winter et al. (1991) *Nature* 349:293; Lobuglio et al. (1989) *Proc. Nat. Acad. Sci. USA* 86:4220; Shaw et al. (1987) *J Immunol.* 138:4534; and Brown et al. (1987) *Cancer Res.* 47:3577; Riechmann et al. (1988) *Nature* 332:323; Verhoeyen et al. (1988) *Science* 239:1534; and Jones et al. (1986) *Nature* 321:522; EP Publication No. 519,596, published 23 Dec. 1992; and U.K. Patent Publication No. GB 2,276,169, published 21 Sep. 1994).

Antibody molecule fragments, e.g., $F(ab')_2$, Fv, and sFv molecules, that are capable of exhibiting immunological binding properties of the parent monoclonal antibody molecule can be produced using known techniques. Inbar et al. (1972) *Proc. Nat. Acad. Sci. USA* 69:2659; Hochman et al. (1976) *Biochem* 15:2706; Ehrlich et al. (1980) *Biochem* 19:4091; Huston et al. (1988) *Proc. Nat. Acad. Sci. USA* 85(16):5879; and U.S. Pat. Nos. 5,091,513 and 5,132,405, to Huston et al.; and 4,946,778, to Ladner et al.

In the alternative, a phage-display system can be used to expand monoclonal antibody molecule populations in vitro. Saiki, et al. (1986) *Nature* 324:163; Scharf et al. (1986) *Science* 233:1076; U.S. Pat. Nos. 4,683,195 and 4,683,202; Yang et al. (1995) *J Mol Biol* 254:392; Barbas, III et al. (1995) *Methods: Comp. Meth Enzymol* 8:94; Barbas, III et al. (1991) *Proc Natl Acad Sci USA* 88:7978.

Once generated, the phage display library can be used to improve the immunological binding affinity of the Fab molecules using known techniques. See, e.g., Figini et al. (1994) *J. Mol. Biol.* 239:68. The coding sequences for the heavy and light chain portions of the Fab molecules selected from the phage display library can be isolated or synthesized, and cloned into any suitable vector or replicon for expression. Any suitable expression system can be used, including those described above.

Polynucleotide sequences encoding the rabbit monoclonal antibodies and immunoreactive fragments thereof, described above, are readily obtained using standard techniques, well known in the art, such as those techniques described above with respect to the HBsAgs.

Antibodies which are directed against HBV epitopes, are particularly useful for detecting the presence of HBV or HBV antigens in a sample, such as a serum sample from an HBV-infected human. An immunoassay for an HBV antigen may utilize one antibody or several antibodies either alone or in combination with HBV antigens. An immunoassay for an HBV antigen may use, for example, a monoclonal antibody directed towards an HBV epitope, a combination of monoclonal antibodies directed towards epitopes of one HBV polypeptide, monoclonal antibodies directed towards epitopes of different HBV polypeptides, polyclonal antibodies directed towards the same HBV antigen, polyclonal antibodies directed towards different HBV antigens, or a combination of monoclonal and polyclonal antibodies. For example, both rabbit and mouse monoclonal antibodies can be used in the subject assays. Immunoassay protocols may be based, for example, upon competition, direct reaction, or sandwich type assays using, for example, labeled antibody and are described further below. The labels may be, for example, fluorescent, chemiluminescent, or radioactive.

The anti-HBV antibodies may further be used to isolate HBV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HBV particles or antigens from a biological sample, such as blood or plasma. The bound HBV particles or antigens are recovered from the column matrix by, for example, a change in pH.

Preferred anti-HBV antibodies are those produced by the hybridoma cell lines 99S9 (CMCC #12336) and 99S6 (CMCC #12337) (ATCC Accession Nos. PTA-6014 and PTA-6015, respectively) as well as antibody fragments (e.g. Fab, F(ab')2, Fv, sFv) and chimeric or humanized antibodies derived thereform.

HBV Diagnostic Assays

As explained above, the anti-HBV antibodies produced as described above, can be used in assays to identify HBV infection. The anti-HBV antibodies can be used as either the capture component and/or the detection component in the assays, as described further below. Thus, the presence of HBV in a biological sample can be determined by the presence of HBV antigens and/or anti-HBV antibodies as an indicator of HBV in the sample. The monoclonal antibodies can be used for detecting HBV in blood samples, including without limitation, in whole blood, serum, platelets, and plasma. The antibodies can be used to detect HBV infection in a subject, such as a human subject, as well as to detect HBV contamination in donated blood samples by detecting the presence of HBV antigens, particularly HBsAgs, and HBV antibodies, depending on the assay used. Thus, aliquots from individual donated samples or pooled samples can be screened for the presence of HBV and those samples or pooled samples contaminated with HBV can be eliminated before they are combined. In this way, a blood supply substantially free of HBV contamination can be provided. By "substantially free of HBV" is meant that the presence of HBV is not detected using the assays described herein. Similarly, the methods of the present invention can be used to screen potential tissue and organ samples for transplantation and contaminated tissues and organs can be discarded.

Assays for use herein include Western blots; agglutination tests; enzyme-labeled and mediated immunoassays, such as ELISAs; biotin/avidin and biotin-streptavidin type assays; protein A- or protein G-mediated immunoassays; radioimmunoassays; immunoelectrophoresis; immunoprecipitation, strip immunoblot assays, and the like. The reactions generally include detectable labels such as fluorescent, chemiluminescent, radioactive, enzymatic labels or dye molecules, or other methods for detecting the formation of a complex between the HBV antigen present in the sample and antibody or antibodies contacted therewith.

The aforementioned assays generally involve separation of unbound antibodies or antigen in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In one aspect of the invention, the anti-HBsAg antibodies, such as the rabbit monoclonal antibodies described herein, are used for capture or detection or both of HBV antigens, particularly HBsAgs, in a sample. Antibodies to the HBsAgs, produced as described above, can be used for the capture or detection or both of HBV antigens in a sample. By "capture" of an analyte ( here HBV antigens in a sample) is meant that the analyte can be separated from other components of the sample by virtue of the binding of the capture molecule. Typically, the capture molecule is associated with a solid support, either directly or indirectly. Typically, the detection molecule is associated with a detectable label, either directly or indirectly.

Typically, a solid support is first reacted with a solid phase component (e.g., one or more of the anti-HBV antibodies) under suitable binding conditions such that the component is sufficiently immobilized to the support. Sometimes, immobilization to the support can be enhanced by first coupling to a protein with better binding properties. Suitable coupling proteins include, but are not limited to, protein A or protein G, macromolecules such as serum albumins including bovine serum albumin (BSA), keyhole limpet hemocyanin, immunoglobulin molecules, thyroglobulin, ovalbumin, and other proteins well known to those skilled in the art. Alternatively, a streptavidin- or avidin-coated solid support can be used to immobilize a biotinylated antibody. Other molecules that can be used to bind the antibody to the support include polysaccharides, polylactic acids, polyglycolic acids, polymeric amino acids, amino acid copolymers, and the like. Such molecules and methods of coupling these molecules are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing the analyte (e.g., HBV antigens) under suitable binding conditions. After washing to remove any non-bound analyte, a secondary binder moiety can be added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated, directly or indirectly, with the rabbit anti-HBV antibodies according to the present invention. Rabbit anti-HBV antibodies directed against one or more HBV mutants as described above can be used. Preferably the rabbit monoclonal antibodies produced by the hybridoma line 99S9 or 99S6 are used. Additionally, other anti-HBV antibodies directed against wild-type HBsAgs can also be present, as can additional mouse monoclonal antibodies directed against a wild-type HBsAg or an HBsAg mutant. A biological sample containing or suspected of containing HBV antigens is then added to the coated wells. After a period of incubation sufficient to allow antigen-antibody binding, the plate(s) can be washed to remove unbound moieties and a detectably labeled secondary binding molecule added. The secondary binding molecule is allowed to react with any captured sample, the plate washed and the presence of the secondary binding molecule detected using methods well known in the art.

In one particular format, an ELISA antigen sandwich format is used. In this case, the solid support is coated with anti-HBV antibodies directed against one or more HBV mutants as described above. Anti-HBV antibodies directed against wild-type HBsAgs can also be present. The sample is then contacted with the support under conditions that allow HBV antigens, if present, to bind one or more or the antibodies to form an antigen/antibody complex. Unbound antigens are removed and an enzyme-labeled antibody that reacts with the bound antigen/antibody complex, such as a labeled anti- HBsAg antibody, is added. An enzyme substrate is used to generate a signal. In this particular embodiment, the anti-HBV antibodies that are coated on the solid support can be rabbit monoclonal antibodies of the present invention, preferably the antibodies produced by hybridoma 99S9 or hybridoma 99S6, or both. Alternatively, or in addition, the detectably labeled antibody can be a rabbit monoclonal antibody of the present invention, preferably the antibodies produced by hybridoma 99S9 or hybridoma 99S6, or both.

In another embodiment, the presence of bound HBV analytes from a biological sample can be readily detected using a secondary binder comprising an antibody directed against the antigen ligands. A number of anti-human immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

The rabbit anti-HBV antibodies of the invention can also be used in an indirect ELISA, for example, an indirect IgG ELISA, as follows. The antibodies specific for HBV surface antigens are attached to a solid support. Protein A or protein G can be used to immobilize the antibodies on the solid support. The support is then contacted with HBsAg under conditions that allow binding to the anti-HBV antibodies bound to the support to form antibody/antigen complexes. Unbound antigens are removed and the support is contacted with a sample to be tested for the presence of human IgG to HBV under conditions that allow binding of human anti-HBV IgG, if present, to the antigens in the antibody/antigen complexes. The presence of bound anti-HBV IgG can be detected using a detectably labeled anti-human IgG antibody. In like manner, the presence of human IgM to HBV can be detected by using labeled anti-human IgM to bind to the antibody/antigen complexes.

The rabbit anti-HBV antibodies of the invention can also be used in a capture ELISA, for example, an IgM capture ELISA, as follows. Anti-human IgM antibodies (e.g., goat anti-human IgM antibodies) are attached to a solid support, the support is contacted with a sample to be tested for the presence of human IgM to HBV, under conditions that would allow the binding of the anti-HBV IgM, if present, to one or more of the anti-human IgM antibodies attached to the solid support, to form antibody/antibody complexes. The HBsAgs (e.g., mutant and/or wild-type) are added under conditions that would allow binding to the anti-HBV IgM in the antibody/antibody complexes forming an antibody/antibody/antigen complex. Unbound antigens are removed and detectably labeled anti-HBV antibodies, produced as described above, are added under conditions that allow binding to the bound antigens. The presence of IgM to HBV in the sample is determined by the presence of the detectably labeled anti-HBV antibodies to the bound anti-human IgM Ab/human anti-HBV IgM/antigen complexes attached to the solid support.

While some of the foregoing assay formats are termed "ELISA" (Enzyme Linked ImmunoSorbant Assay) assays, it will be apparent to one of skill in the art that the use of a detectable label other than an "enzyme linked" binding moiety is possible and may be desirable in many situations. Other suitable detectable labels are described herein and are well known in the art.

Assays can also be conducted in solution, such that the HBV antigens or antibodies and ligands specific for these molecules form complexes under precipitating conditions. In one particular embodiment, the molecules can be attached to a solid phase particle (e.g., an agarose bead or the like) using coupling techniques known in the art, such as by direct chemical or indirect coupling. The coated particle is then contacted under suitable binding conditions with a biological sample suspected of containing HBV antibodies or antigens. Crosslinking between bound antibodies causes the formation of complex aggregates which can be precipitated and separated from the sample using washing and/or centrifugation. The reaction mixture can be analyzed to determine the presence or absence of complexes using any of a number of standard methods, such as those immunodiagnostic methods described above.

In yet a further embodiment, an immunoaffinity matrix can be provided, wherein, for example, a polyclonal population of antibodies from a biological sample suspected of containing HBV antibodies is immobilized to a substrate. An initial affinity purification of the sample can be carried out using immobilized antigens. The resultant sample preparation will thus only contain anti-HBV moieties, avoiding potential non-specific binding properties in the affinity support. A number of methods of immobilizing immunoglobulins (either intact or in specific fragments) at high yield and good retention of antigen binding activity are known in the art. For example, protein A or protein G can be used to immobilize immunoglobulin molecules to the solid support. Once the immunoglobulin molecules have been immobilized to provide an immunoaffinity matrix, HBV antigens, such as HBsAgs, are contacted with the bound antibodies under suitable binding conditions. After any non-specifically bound HBV antigen has been washed from the immunoaffinity support, the presence of bound antigen can be determined by assaying for label using methods known in the art. For example, an enzymatically labeled antibody that reacts with the bound antigen/antibody complex, such as a labeled anti-HBsAg antibody, produced as described above, is added. An enzyme substrate is used to generate a signal.

In another embodiment of the invention, a strip immunoblot assay (SIA) is used to detect HBV antigens in a biological sample. For example, one or more of the rabbit monoclonal antibodies described above, and optionally mouse monoclonal antibodies directed against an HBsAg, can be immobilized on the test strip as capture reagents. SIA techniques are well known in the art and combine traditional western and dot blotting techniques, e.g., the RIBA® (Chiron Corp., Emeryville, Calif.) SIA. In these assays, the antibodies are immobilized as individual, discrete portions, e.g., as bands or dots, on a membranous support, or may be immobilized as a mixture in a single portion. Thus, by "discretely immobilized" on a membrane support is meant that the antibodies are present as separate components and not mixed, such that reactivity or lack thereof with each of the capture reagents present can be assessed. A biological sample suspected of containing HBV antigens is then reacted with the test membrane. Visualization of reactivity in the biological sample can be accomplished using anti-HBV antibody enzyme-conjugates in conjunction with a colorimetric enzyme substrate. Alternatively, the rabbit monoclonal antibodies described above can be used for visualization of the bound antibody-antigen complexes. The test strip for this alternative embodiment may be prepared using, e.g., mouse monoclonal antibodies directed against HBsAg. The assay can be performed manually or used in an automated format.

Solid supports which can be used in the practice of the strip immunoblot assays include, but are not limited to, membrane supports derived from a number of primary polymers including cellulose, polyamide (nylon), polyacrylonitrile, polyvinylidene difluoride, polysulfone, polypropylene, polyester, polyethylene and composite resins consisting of combinations or derivatives of the above. Particularly preferred are supports derived from cellulose, such as nitrocellulose membranes, as well as nylon membranes. The substrate generally includes the desired membrane with an inert plastic backing as a support.

The above-described assay reagents, including the rabbit monoclonal antibodies and/or the HBsAgs described herein, the solid supports with bound reagents, as well as other detection reagents, can be provided in kits, with suitable instructions and other necessary reagents, in order to conduct the assays as described above. The kit may also include control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of Rabbit Monoclonal Antibodies

To produce monoclonal antibodies that confer sufficient immunoreactivities to the various mutants of interest as well as to the wild-type HBsAg, three white female adult New Zealand rabbits were immunized with wild-type HBsAg (adw) and (ayw) antigens (shown in FIGS. 2A and 2B, respectively), followed by boosts every two weeks with a cocktail of the wild-type antigens and five major HBV recombinant mutant antigens, designated D1 (having an A for F substitution at amino acid position 134), D2 (having an S for F substitution at amino acid position 134), D3 (having an R for G substitution at amino acid 145), Y1 (having an L for S substitution at amino acid 143, and Y2 (having an R for Q substitution at amino acid 129 and a T for M substitution at amino acid 133).

The immune B cells from the spleen of the most immunoreactive rabbit were fused to rabbit plasmacytoma cells to produce hybridomas, essentially as described in Spieker-Polet et al., *Proc. Natl. Acad. Sci. USA* (1995) 92:9348-9352. Briefly, 1.5-3×$10^8$ lymphocytes from an immunized rabbit were fused with a fusion partner derived from a rabbit plasmacytoma cell line (for example, 240E 1-1-2, described in U.S. Pat. No. 5,675,063, incorporated herein by reference in its entirety; Spieker-Polet et al., *Proc. Natl. Acad. Sci. USA* (1995) 92:9348-9352) at a ratio of 2:1 with 50% PEG 4000 at 37 C in serum-free medium. The cells were distributed in 96-well cell culture plates at approximately 1×$10^5$ lymphocytes per well, in medium with 15% FBS (or FCS). After 48 hr, HAT medium was added. Medium was changed 2-3 times before screening. Usually, hybridoma colonies were ready for screening in 3-5 weeks. Supernatants were tested for the presence of antibody specific for the immunogen, by ELISA. Immunohistochemistry was used as a secondary screening assay. The hybridomas were sub-cloned by limit dilution. For feeder cells, the fusion partner at 2×$10^4$ cells per well was used.

A total of 3000 clones were screened, and 38 clones (Table 1) were identified as potential candidates for further study. These clones were then subcloned and tested for the production of antibodies with the best reactivity against all seven HBV surface antigens used for the antigen cocktail, both mutant and wild-types (see Table 1). The results indicated that of the 38 clones evaluated, 4 clones (as highlighted in Table 1) had the broadest immunoreactivities to HBsAg mutants. Thus, these 4 HBV rabbit hybridomas were scaled up, purified and further evaluated.

After extensive analyses of the selected 38 HBV hybridoma clones, two clones, 99S9 (ATCC Accession No. PTA-6014) and 99S6 (ATCC Accession No. PTA 6015), were demonstrated to produce antibodies with very broad immunoreactivities against the HBV surface Ag mutant panel. In particular, an ELISA was used to compare the immunoreactivity of two mouse monoclonal antibodies, mMAb1 and mMAb2 (mouse monoclonal antibodies directed against HBsAg) and the rabbit monoclonal antibodies produced by the 99S9 and 99S6 hybridoma cell lines with the various mutant HBsAgs described above. Additionally, the mouse monoclonal antibodies and rabbit monoclonal antibodies from hybridomas 99S6 and 99S9 were tested using a BIACORE 3000 system (Biacore AB, Piscataway, N.J.). This system provides real-time biomolecular interaction analysis (BIA) using surface plasmon resonance (SPR) technology. SPR-based biosensors monitor interactions by measuring the mass concentration of biomolecules close to a surface. The surface is made specific by attaching one of the interacting partners. Sample containing the other partner(s) flows over the surface. When molecules from the sample bind to the interactant attached to the surface, the local concentration changes and an SPR response is measured. The response is directly proportional to the mass of molecules that bind to the surface. In this case, Goat anti-rabbit IgG antibody (to test immunoreactivity of the rabbit monoclonal antibodies) or goat anti-mouse IgG (to test immunoreactivity of the mouse monoclonal antibodies) was immobilized on a sensor chip to provide the surface-capturing antibodies. The rabbit or mouse monoclonal antibodies described above (ligands) were then captured by the surface capturing antibodies. The mutant and wild-type HBsAgs (analytes) were then passed through this surface and the antibody/antigen interactions were detected and measured using a BIACORE SPR optical device.

FIGS. 3A-3D and Table 2 summarize the BIACORE analysis results of rabbit monoclonal antibodies from 99S6 (FIG. 3B) and 99S9 (FIG. 3D), in comparison with the mouse antibodies mMAb1 (FIG. 3C) and mMAb2 (FIG. 3A). For these and the following studies, a number of different mouse monoclonal antibodies to HBsAg were used (mMAb1, mMAb2, mMAb3, mMAb4, mMAb5, and mMAb6). Several commercially available mouse monoclonal antibodies were also used. As shown in FIGS. 3A-3D, while mouse monoclonal antibody mMAb2 was deficient in binding to the mutant D3, and mMAb1 was deficient in binding to mutants D3 and Y1, both rabbit hybridoma clones 99S9 and 99S6 produced antibodies with significant binding activities to all 7 antigens, including to D3 and Y1. In addition, the BIACORE results also evidenced that binding of rabbit monoclonal antibodies (from hybridoma clones 99S9 and 99S6) to the mutants D3 and Y1 was very stable (FIG. 3). These results demonstrated that the rabbit monoclonal antibodies from clones 99S9 and 99S6 had much stronger immunoreactivities against mutant antigens D3 and Y1 while retaining immunoreactivities for the other antigens, and thus demonstrated that the rabbit antibodies had much broader immunoreactivities for the various HBsAg mutants compared to the two mouse monoclonal antibodies.

To further demonstrate the advantages of the rabbit monoclonal antibodies for HBV variant (i.e., mutant) detection, the rabbit monoclonal antibody from 99S9 was tested in comparison with the mouse monoclonal antibodies as the capture or as the detection antibody in sandwich ELISA assays for detection of the wild-type and variants of HBsAg. In these experiments, two sets of ELISA plates were coated with either single rabbit monoclonal antibody (99S9) or a cocktail of two anti-HBsAg mouse monoclonal antibodies, mMAb2 and 160S11 (BD Biosciences Pharmingen (San Diego, Calif.). These two sets of capture plates were paired with a single 99S9 horseradish peroxidase (HRP) detection system, or paired with a mouse monoclonal antibody cocktail containing a mixture of 4 HRP-labeled anti-HBsAg MAbs (mMAb1, M01077 (Fitzgerald Industries International, Concord, Mass.), M01079 (Fitzgerald Industries International, Concord, Mass.), and mMAb3).

The results were consistent with the results from the BIACORE analysis study. The rabbit monoclonal antibody from 99S9 had broader immunoreactivities compared with the mouse monoclonal antibodies. When 99S9 was tested as the sole capture and detection antibody (99S9 as the capture antibody and HRP-99S9 as the detection antibody), it was capable of detecting all 7 antigens, while the mouse monoclonal antibody cocktails (mMAb2/160S11 as the capture antibody and HRP-mMAb1/M77/M79/2D11 as the detection antibody) failed to detect D3 antigen (Table 3). These results showed that a single rabbit monoclonal antibody could sufficiently replace the multiple mouse monoclonal antibodies in ELISA assays used for detection of some major escaped mutants.

To summarize the above experiments, rabbit monoclonal antibody 99S9 had affinity to 7 antigens tested and showed much slower off-rates for all of them, especially for D3 and Y1 (FIG. 3 and Table 2). Although the mouse monoclonal mMAb1 seemed to have significantly higher affinity for mutant D1, D2, and wild-types adw and ayw, it was incapable of binding to mutant antigens D3 and Y1 (FIG. 3 and Table 2). The mouse monoclonal antibody mMAb2 had overall lower affinities for the most HBV mutant antigens and was incapable of binding to mutant antigen D3 (FIG. 3 and Table 2). The rabbit monoclonal antibody 99S9 alone was sufficient to replace the combinations of multiple mouse monoclonal antibodies for more effective capture and/or detection of mutant D3 (Table 3).

To test the ability of the rabbit monoclonal antibodies to detect other HBsAg variants, additional ELISAs were carried out using either only mouse monoclonal antibodies against HBsAg (mMAb ELISA) or a combination of mouse monoclonals and rabbit monoclonals against HBsAg (rMAb ELISA). For the mMAb ELISA, 5 different anti-HBsAg mouse monoclonal antibodies were used, 2 for capture (mMAb2 and mMAb4) and 3 for detection (mMAb1, mMAb5 and mMAb6). For the rMAb ELISA, 2 of the mouse monoclonal antibodies used for detection (mMAb5 and mMAb6) were replaced by a single rabbit monoclonal antibody (99S9). The capture antibodies were biotinylated and immobilized on streptavidin-coated wells. The detection antibodies were conjugated with horseradish peroxidase (HRP). Table 4 shows the results with a number of HBsAg variants. The rMAb ELISA detected all of the variants that were detected in the mMAb ELISA and, additionally, detected 2 variants that were not detected in the mMAb ELISA, the P120Q variant and the P142S variant. Thus, the ELISA using the rabbit monoclonal antibody (99S9) was able to detect more HBsAg variants using fewer antibodies than the ELISA using only the mouse monoclonal antibodies.

Therefore, rabbit monoclonal antibodies provide a powerful tool for better detection of HBV variant antigens.

Thus, novel monoclonal antibodies and methods for detecting HBV infection are disclosed. Although preferred embodiments of the subject invention have been described in some detail, it is understood that obvious variations can be made without departing from the spirit and the scope of the invention as described herein.

TABLE 1

| | HBV Mutant Antigens | | | | | HBV Wild-type Antigens | |
|---|---|---|---|---|---|---|---|
| ID | D1 | D2 | D3 | Y1 | Y2 | ADW | AYW |
| 27S-2 | 2.95 | 2.96 | 2.75 | 0.70 | 1.06 | 3.30 | 0.75 |
| 64S1 | 0.14 | 0.13 | 0.07 | 0.00 | 0.00 | 0.10 | 0.00 |
| 64S2 | 0.00 | 0.00 | 0.00 | 0.00 | 0.00 | 0.00 | 0.00 |
| 64S3 | 0.05 | 0.04 | 0.01 | 0.00 | 0.00 | 0.02 | 0.00 |
| 64S4 | 0.00 | 0.00 | 0.00 | 0.01 | 0.00 | 0.00 | 0.00 |
| 71S1 | 2.24 | 1.90 | 1.40 | 0.05 | 0.06 | 1.70 | 0.07 |
| 71S4 | 3.07 | 2.90 | 2.70 | 0.21 | 0.22 | 2.80 | 0.24 |
| 71S5 | 3.38 | 3.40 | 3.20 | 0.29 | 0.35 | 3.00 | 0.35 |
| 71S7 | 0.00 | 0.00 | 0.00 | 0.00 | 0.00 | 0.00 | 0.00 |
| 71S8 | 0.00 | 0.00 | 0.00 | 0.00 | 0.00 | 0.00 | 0.00 |
| 71S12 | 0.00 | 0.00 | 0.00 | 0.00 | 0.00 | 0.00 | 0.00 |
| 71S14 | 3.06 | 0.00 | 3.20 | 0.32 | 0.32 | 3.00 | 0.34 |
| 71S15 | 2.93 | 3.10 | 3.00 | 0.28 | 0.26 | 2.70 | 0.30 |
| 71S16 | 3.13 | 3.00 | 2.98 | 0.32 | 0.35 | 3.30 | 0.40 |
| 71S17 | 3.33 | 3.30 | 2.77 | 0.38 | 0.48 | 3.00 | 0.53 |
| 96S1 | 3.45 | 3.40 | 2.87 | 3.10 | 3.30 | 2.70 | 2.92 |
| 99S1 | 3.37 | 2.80 | 2.90 | 1.40 | 1.50 | 2.90 | 1.70 |
| 99S4 | 2.78 | 2.70 | 2.40 | 0.73 | 0.80 | 3.00 | 1.20 |
| 99S6 | 3.01 | 3.20 | 2.60 | 1.05 | 1.20 | 3.30 | 1.45 |
| 99S7 | 2.21 | 1.99 | 1.80 | 0.40 | 0.54 | 2.40 | 0.78 |
| 99S8 | 2.58 | 2.30 | 2.30 | 0.60 | 0.66 | 2.70 | 0.90 |
| 99S9 | 3.62 | 2.80 | 2.80 | 1.40 | 1.40 | 2.80 | 1.68 |
| 99S10 | 2.50 | 2.40 | 2.30 | 0.80 | 0.90 | 2.50 | 1.06 |
| 116S1 | 3.20 | 3.30 | 0.00 | 2.50 | 2.40 | 2.30 | 2.80 |
| 116S2 | 2.30 | 1.90 | 0.01 | 1.70 | 1.60 | 2.44 | 1.99 |
| 116S3 | 2.70 | 2.60 | 0.00 | 2.40 | 1.98 | 2.60 | 2.70 |
| 116S4 | 2.80 | 2.60 | 0.00 | 2.20 | 1.87 | 2.80 | 2.45 |
| 116S5 | 1.90 | 1.70 | 0.00 | 1.60 | 1.30 | 2.01 | 2.03 |
| 121S2 | 3.07 | 2.96 | 2.90 | 0.33 | 0.00 | 3.07 | 2.40 |
| 121S4 | 3.70 | 3.10 | 2.90 | 0.36 | 0.00 | 3.20 | 2.60 |
| 121S5 | 3.01 | 2.70 | 2.90 | 0.31 | 0.00 | 2.80 | 2.10 |
| 121S6 | 3.70 | 3.40 | 2.80 | 0.42 | 0.00 | 3.10 | 2.60 |
| 121S8 | 2.80 | 3.00 | 3.00 | 1.48 | 0.10 | 2.90 | 2.70 |
| 121S9 | 3.20 | 3.20 | 2.90 | 0.27 | 0.06 | 2.90 | 1.80 |
| 123S3 | 1.65 | 2.10 | 0.01 | 0.00 | 1.70 | 0.00 | 0.00 |
| 123S4 | 1.45 | 1.70 | 0.01 | 0.00 | 1.40 | 0.00 | 0.00 |
| 123S8 | 1.00 | 1.30 | 0.00 | 0.02 | 1.10 | 0.00 | 0.00 |
| 123S12 | 1.05 | 1.40 | 0.00 | 0.02 | 1.10 | 0.00 | 0.00 |

Capture: ELISA plates were coated with the 7 different antigens.
Sample Size: 200 μl (1:100 dilution of cell culture in the specimen diluent).
Detection: Goat anti rabbit (fab)'2-HRP conjugate.

TABLE 2

| | | ELISA | BIACORE | | | |
|---|---|---|---|---|---|---|
| HBV | Mutation | mMAb2/ | Mouse mAb | | Rabbit mAb | |
| recombinant | Site | mMAb1 | (mMAb1) | (mMAb2) | (99S6) | (99S9) |
| D1 | F134A | ++ | +++++ | + | ++ | + |
| D2 | F134S | ++ | +++++ | ++ | ++ | + |
| D3 | G145R | (−, +/−, −) | − or +/− | − | + | + |
| Y1 | S143L | (−, −) | − | + | + | + |
| Y2 | 129Q/133T | +++ | no result | no result | no result | no result |
| HBV Wild-type | Mutation Site | mMAb2/ mMAb1 | (mMAb1) | (mMAb2) | (99S6) | (99S9) |
| adw | | +++ | +++++ | ++ | + | ++ |
| ayw | | + | +++++ | + | + | + |

TABLE 3

| | Capture: | | | |
|---|---|---|---|---|
| | 2 Mouse MnAbs mMAb2/160S11 | | 1 Rabbit MnAb99S9 | |
| | Detection | | | |
| | 4 Mouse MnAbs mMAb1/M77/M79/ mMAb3 | 1 Rabbit MnAb 99S9-HRP | 4 Mouse MnAbs mMAb1/M77/M79/ mMAb3 | 1 Rabbit MnAb 99S9-HRP |
| Testing samples | OD | OD | OD | OD |
| Adw (3 ng/test) | 2.84 | 0.73 | 2.45 | 0.53 |
| Ayw (3 ng/test) | 2.64 | 0.31 | 2.67 | 0.31 |
| D1 (3 ng/test) | 2.35 | 0.56 | 2.02 | 0.37 |
| D2 (3 ng/test) | 1.90 | 0.56 | 1.69 | 0.46 |
| D3 (3 ng/test) | 0.02 | 0.08 | 0.01 | 0.05 |
| Y1 (3 ng/test) | 0.87 | 0.30 | 0.81 | 0.21 |
| Y2 (3 ng/test) | 1.69 | 0.32 | 1.25 | 0.20 |
| P120Q (A)(3 ng/test) | 1.65 | 0.17 | 1.00 | 0.07 |
| Cut Off | 0.07 | 0.09 | 0.01 | 0.03 |
| Testing samples | S/C | S/C | S/C | S/C |
| adw (3 ng/test) | 40.6 | 8.1 | 244.5 | 17.8 |
| ayw (3 ng/test) | 38.2 | 3.5 | 266.7 | 10.2 |
| D1 (3 ng/test) | 33.6 | 6.2 | 201.9 | 12.2 |
| D2 (3 ng/test) | 27.2 | 6.2 | 168.8 | 15.2 |
| D3 (3 ng/test) | 0.3 | 0.9 | 0.9 | 1.8 |
| Y1 (3 ng/test) | 12.4 | 3.3 | 80.6 | 7.0 |
| Y2 (3 ng/test) | 24.1 | 3.5 | 125.3 | 6.6 |
| P120Q (A)(3 ng/test) | 23.6 | 1.9 | 99.7 | 2.3 |

Capture 1: rabbit Monoclonal 99S9 Capture 2: Mouse Monoclonals mMAb2, 160S11
Detection 1: mMnAb-HRP (mMAb1, M01077, M01079, mMAb3) Detection 2: rabbit MnAb-HRP 99S9

TABLE 4

| | ALU | |
|---|---|---|
| Sample | Mouse MAb Assay | Rabbit MAb Assay |
| Positive Control | 127.15 | 143.06 |
| Negative Control | 3.34 | 4.42 |
| adw 0.5 ng/ml | 327.62 | 334.99 |
| ayw 0.5 ng/ml | 299.61 | 302.06 |
| G145R 1 ng/ml | 167.36 | 145.65 |
| S143L 1 ng/ml | 33.59 | 39.67 |
| P120Q 1 ng/ml | 33.06 | 68.81 |
| P142L 0.2 ng/ml | 21.01 | 35.77 |
| D144A 0.2 ng/ml | 48.40 | 37.54 |
| F134S 0.2 ng/ml | 85.83 | 88.22 |
| F134A 0.2 ng/ml | 140.45 | 145.80 |
| Y118K 1:9000 | 26.83 | 28.68 |
| Y118S 1:9000 | 46.65 | 49.10 |
| Y131A 1:9000 | 85.89 | 86.72 |
| T126N (Neat) | 156.28 | 166.39 |
| Q129H (Neat) | 222.93 | 291.02 |
| M133D (Neat) | 51.13 | 66.07 |

TABLE 4-continued

| | ALU | |
|---|---|---|
| Sample | Mouse MAb Assay | Rabbit MAb Assay |
| P142S (1:10 Dil) | 41.48 | 223.58 |
| D144N (1:600 Dil) | 61.55 | 81.05 |

Deposits of Strains Useful in Practicing the Invention

A deposit of biologically pure cultures of the following strains was made with the American Type Culture Collection (ATCC), 10801 University Boulevard, Manassas, Va. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 U.S.C. §122 and the Commissioner's rules pursuant thereto (including 37 C.F.R. §1.12). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Hybridoma | Deposit Date | ATCC No. |
|---|---|---|
| 99S6 (CMCC #12337) | May 26, 2004 | PTA-6015 |
| 99S9 (CMCC #12336) | May 26, 2004 | PTA-6014 |

The invention claimed is:

1. A hybridoma selected from Hybridoma 99S6 (ATCC Accession number PTA-6015) or Hybridoma 99S9 (ATCC Accession number PTA-6014).

2. An antibody produced by the hybridoma of claim 1.

3. A rabbit monoclonal antibody that recognizes the same epitope as an antibody produced by hybridoma 99S6 (ATTC Accession No. PTA-6015) or 99S9 (ATCC Accession No. PTA-60 14).

4. A solid support comprising at least one rabbit monoclonal antibody according to either of claims 2 or 3.

5. The solid support of claim 4, wherein the support further comprises one or more additional antibodies directed against a wild-type HBsAg or an HBsAg mutant with a mutation in the "a" determinant region.

6. The solid support of claim 5, wherein the one or more additional antibodies comprise an additional monoclonal antibody.

7. The solid support of claim 6, wherein the one or more additional antibodies comprise a mouse monoclonal antibody.

8. The solid support of claim 4, further comprising at least two internal controls, wherein one of the controls defines the lower detection limit for a positive result in an immunoassay using the solid support and the other control defines a highly positive result in an immunoassay using the solid support.

9. The solid support of claim 4, wherein the solid support is a nitrocellulose strip.

* * * * *